United States Patent
Harada et al.

(10) Patent No.: US 11,434,563 B2
(45) Date of Patent: Sep. 6, 2022

(54) RAW MATERIAL FOR CHEMICAL DEPOSITION CONTAINING RUTHENIUM COMPLEX, AND CHEMICAL DEPOSITION METHOD USING THE RAW MATERIAL FOR CHEMICAL DEPOSITION

(71) Applicant: TANAKA KIKINZOKU KOGYO K.K., Tokyo (JP)

(72) Inventors: Ryosuke Harada, Tsukuba (JP); Teruhisa Iwai, Tsukuba (JP); Toshiyuki Shigetomi, Tsukuba (JP); Shigeyuki Ootake, Tsukuba (JP); Seung-Joon Lee, Tsukuba (JP)

(73) Assignee: TANAKA KIKINZOKU KOGYO K.K., Tokyo (JP)

( * ) Notice: Subject to any disclaimer, the term of this patent is extended or adjusted under 35 U.S.C. 154(b) by 0 days.

(21) Appl. No.: 17/299,294

(22) PCT Filed: Dec. 2, 2019

(86) PCT No.: PCT/JP2019/046935
§ 371 (c)(1),
(2) Date: Jun. 2, 2021

(87) PCT Pub. No.: WO2020/116364
PCT Pub. Date: Jun. 11, 2020

(65) Prior Publication Data
US 2022/0018018 A1 Jan. 20, 2022

(30) Foreign Application Priority Data
Dec. 3, 2018 (JP) .............................. JP2018-226173

(51) Int. Cl.
*C23C 16/18* (2006.01)
(52) U.S. Cl.
CPC .................................. *C23C 16/18* (2013.01)

(58) Field of Classification Search
CPC ....................................................... C23C 16/18
See application file for complete search history.

(56) References Cited

U.S. PATENT DOCUMENTS 6,476,247 B1 11/2002 Okamoto et al.
2012/0177845 A1 7/2012 Odedra et al.
(Continued)

FOREIGN PATENT DOCUMENTS

JP 2001-163894 A 6/2001
JP 2013-501714 A 1/2013
(Continued)

OTHER PUBLICATIONS

Kawano et al., "Ligand Structure Effect on a Divalent Ruthenium Processor for MOCVD," Mater.res.Soc.Symp.Proc., vol. 1155, 2009, pp. 35-41.
(Continued)

*Primary Examiner* — Elizabeth A Burkhart
(74) *Attorney, Agent, or Firm* — Foley & Lardner LLP

(57) ABSTRACT

The present invention relates to a raw material for chemical deposition for producing a ruthenium thin film or a ruthenium compound thin film by a chemical deposition method, containing a ruthenium complex represented by the following Chemical Formula 1. In Chemical Formula 1, ligands $L_1$ and $L_2$ coordinated to ruthenium are represented by the following Chemical Formula 2. The raw material for chemical deposition according to the present invention can be formed into a high quality thin film even if a reaction gas containing an oxygen atom is not used.

(Continued)

[Chemical Formula 1]

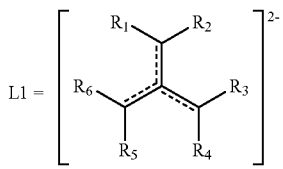

[Chemical Formula 2]

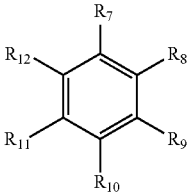

wherein $R_1$ to $R_{12}$, which are substituents of the ligands $L_1$ and $L_2$, are each independently any one of a hydrogen atom, and a linear or branched alkyl group having a carbon number of 1 or more and 4 or less.

8 Claims, 1 Drawing Sheet

(56) References Cited

U.S. PATENT DOCUMENTS

2012/0277456 A1* 11/2012 Doppiu .................. B01J 31/00
556/136

2015/0056384 A1* 2/2015 Gatineau ................. C23C 16/50
427/255.28
2017/0226638 A1* 8/2017 Han ........................ C23C 16/18

FOREIGN PATENT DOCUMENTS

| JP | 2017-524729 A | 8/2017 |
| KR | 2010-0060482 A | 6/2010 |
| WO | WO 2014/030609 * | 2/2014 |

OTHER PUBLICATIONS

Eom et al., "Low Temperature Atomic Layer Deposition of Ruthenium Thin Films Using Isopropylmethylbenzene-Cyclohexadiene-Ruthenium and $O_2$," Electrochemical and Solid-State Letters, vol. 12, No. 11, 2009, pp. D85-D88.

Sari et al., "Plasma Enhanced Atomic Layer Deposition of Ruthenium Thin Films Using Isopropylmethylbenzene-Cyclohexadiene-Ruthenium and $NH_3$ Plasma," Journal of Electrochemical Society, vol. 158, No. 1, 2011, pp. D42-D47.

International Searching Authority, "International Search Report," issued in connection with International Patent Application No. PCT/JP2019/046935, dated Feb. 4, 2020.

International Searching Authority, "Written Opinion," issued in connection with International Patent Application No. PCT/JP2019/046935, dated Feb. 4, 2020.

* cited by examiner

RAW MATERIAL FOR CHEMICAL DEPOSITION CONTAINING RUTHENIUM COMPLEX, AND CHEMICAL DEPOSITION METHOD USING THE RAW MATERIAL FOR CHEMICAL DEPOSITION

CROSS-REFERENCE TO RELATED APPLICATIONS

The present application claims priority under 37 U.S.C. § 371 to International Patent Application No. PCT/JP2019/046935, filed Dec. 2, 2019, which claims priority to and the benefit of Japanese Patent Application No. 2018-226173, filed on Dec. 3, 2018. The contents of these applications are hereby incorporated by reference in their entireties.

TECHNICAL FIELD

The present invention relates to a raw material for chemical deposition for producing a ruthenium thin film or a ruthenium compound thin film by a chemical deposition method such as a CVD method or an ALD method. Specifically, the present invention relates to a raw material for chemical deposition containing a ruthenium complex to which a reducing gas is applicable as a reaction gas.

BACKGROUND ART

Ruthenium (Ru) is a metal that has a low resistance and is thermally and chemically stable, and is a metal useful as an electrode material of various semiconductor devices such as a DRAM, and an FERAM. As a specific form of the electrode material, a thin film formed of ruthenium or a ruthenium compound (hereinafter referred to as a ruthenium-containing thin film) is applied. As a method for producing the ruthenium-containing thin film, a chemical deposition method such as a CVD method (chemical vapor deposition method) or an ALD method (atomic layer deposition method) is generally applied.

As a raw material (precursor) for a chemical deposition method, a compound raw material containing a ruthenium complex is known, and a large number of examinations and reports have been conventionally made on complexes. For example, a ruthenium complex in which cyclopentadiene or a derivative thereof, a cyclopentadienyl ligand, is coordinated to ruthenium has been conventionally well known as a raw material for chemical deposition. Patent Document 1 and Non Patent Document 1 describe bis(ethylcyclopentadienyl)ruthenium represented by Chemical Formula 1, in which two ethylcyclopentadienyls are coordinated to ruthenium.

[Chemical Formula 1]

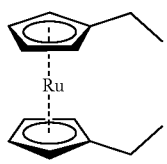

Non Patent Documents 2 and 3 describe a method for producing a ruthenium-containing thin film of (1,3-cyclohexadiene)(1-methyl-4-isopropylbenzene)ruthenium represented by Chemical Formula 2, in which cyclohexadiene and a benzene are coordinated to ruthenium.

[Chemical Formula 2]

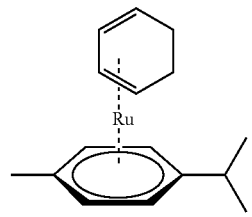

CITATION LIST

Patent Literature

Patent Literature 1: JP 2001-163894 A

Non Patent Literature

Non Patent Literature 1: K. Kawano et al., Materials Research Society Symposium Proceedings 1155-C09-11 (2009)
Non Patent Literature 2: Tae-Kwang Eom et al., Electrochemical and Solid-State Letters, 2009, 12(11), D85-D88
Non Patent Literature 3: W. Sari et al., Journal of the Electrochemical Society, 2011, 158(1), D42-D47

SUMMARY OF INVENTION

Technical Problem

In a chemical deposition method such as a CVD method or an ALD method, a raw material compound containing a ruthenium complex is vaporized, and a raw material gas thus generated is transported onto a substrate in a reactor. Then, the ruthenium complex is decomposed on a surface of the substrate to produce a ruthenium-containing thin film. For the decomposition of the ruthenium complex on the surface of the substrate, heating is generally performed. In addition, in the chemical deposition method, the ruthenium complex having been vaporized and a reaction gas are mixed, and the resultant mixture is used as a raw material gas for film formation in many cases. This is for promoting, in decomposition of the ruthenium complex on the surface of the substrate, the decomposition using an effect of the reaction gas in addition to heating.

The ruthenium complex to be used as a raw material for the chemical deposition method is required to have a high vapor pressure and a stable vaporization characteristic, and to have a high stability enough to be stably transported onto the substrate after the vaporization. The above-described conventional raw material compounds containing the ruthenium complex meet these requirements.

In the ruthenium-containing thin film to be used in various applications and the film formation process described above, substrate oxidation during the film formation and oxide generation (ruthenium oxide) are avoided in some cases. In such cases, it is necessary to select a raw material and film formation conditions in such a manner as to avoid substrate oxidation and oxide generation in a resultant thin film. In this regard, the ruthenium complex used as the conventional raw material for chemical deposition described above does not contain an oxygen atom in its molecular structure, and hence the ruthenium complex itself does not cause oxidation.

In the film formation using the conventional ruthenium complex, however, in order to form a film without contaminating a resultant thin film with impurities, oxygen is mixed as a reaction gas in general. In use of the conventional ruthenium complex, it is not impossible to achieve film formation only by heating, but in this case, carbon or the like contained in a complex ligand is liable to remain in a resultant thin film to cause deterioration of film characteristics such as increase in a specific resistance. Therefore, although oxygen is introduced as a reaction gas, it is concerned that the reaction gas may cause oxidation of a substrate to cause contamination of a thin film to be produced with ruthenium oxide.

As reported in Non Patent Document 3 and the like, a complex can be decomposed without using oxygen but by using excitation energy of plasma or the like. When plasma is used, however, it is concerned that an underlying portion may be damaged. Furthermore, a chemical deposition method using plasma excitation is inferior in simpleness of an apparatus and the like, and the process is difficult to control. Accordingly, as decomposition energy used in a chemical deposition method, it is deemed that heating is preferably mainly used with a reaction gas applied.

Under these circumstances, it is substantially indispensable to apply a reaction gas of oxygen or the like in the conventional film formation using a ruthenium complex. Therefore, it has been difficult to solve the problem of oxidation. In addition to this problem, there is a problem that many of ruthenium complexes described above are highly stable and hence unsuitable to low temperature film formation.

The present invention was devised under the above-described circumstances, and provides a ruthenium complex to be used as a raw material for chemical deposition for producing a ruthenium-containing thin film, with which a high-quality ruthenium-containing thin film can be produced without using a reaction gas containing an oxygen atom such as oxygen.

Solution to Problem

It is deemed that the above-described problems can be solved by finding a ruthenium complex decomposable with a reducing gas such as hydrogen. In this regard, the above-described conventional ruthenium complexes are poor in reactivity to hydrogen or the like, and hence it has been difficult to produce a high quality thin film by heating under a hydrogen atmosphere.

Even if a ruthenium complex decomposable with a reducing gas such as hydrogen is necessary, a complex having excessively low stability is not preferable. In the fields to which the present invention is applied, a ruthenium complex is required to have appropriate stability. It is not always easy to specify a ruthenium complex having reactivity to a specific reaction gas in consideration of stability. In addition, a ruthenium complex of the present invention is also required to meet conditions that no oxygen atom is contained in a molecular structure and that a vaporization characteristic is appropriate.

The present inventors have made earnest studies on a ruthenium complex that has appropriate stability and vaporization characteristic and that is reactive to a reducing gas such as hydrogen. As a result, a ruthenium complex having two ligands, that is, benzene or a derivative thereof and trimethylenemethane or a derivative thereof, was found, and thus, the present invention was accomplished.

Specifically, the present invention is drawn to a raw material for chemical deposition to be used for producing a ruthenium thin film or a ruthenium compound thin film by a chemical deposition method, containing a ruthenium complex represented by the following Chemical Formula 3:

$RuL_1L_2$ [Chemical Formula 3]

Here, a ligand $L_1$ and a ligand $L_2$ coordinated to ruthenium are represented by the following Chemical Formula 4:

[Chemical Formula 4]

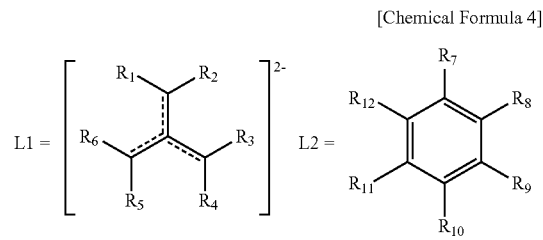

wherein, $R_1$ to $R_{12}$, which are substituents of the ligands $L_1$ and $L_2$, are each independently any one of a hydrogen atom, and a linear or branched alkyl group having a carbon number of 1 or more and 4 or less.

The ruthenium complex that constitutes the raw material for chemical deposition according to the present invention has a characteristic that trimethylenemethane or a trimethylenemethane derivative is applied as a ligand. Trimethylenemethane is a carbohydrate ligand containing carbon and hydrogen but not containing an oxygen atom, and hence is a preferable ligand from the viewpoint of constituent elements. It forms a complex with peculiar coordination geometry to a metal (ruthenium), and has an appropriate bonding force. Therefore, it has effective reactivity also to a reducing gas such as hydrogen. Furthermore, since trimethylenemethane has a low molecular weight, a metal complex that can be easily vaporized can be obtained when it is used as a ligand.

The constitution of the ruthenium complex that constitutes the raw material for chemical deposition according to the present invention having the above-described advantages will be described in detail.

In the ruthenium complex applied in the present invention, trimethylenemethane or a trimethylenemethane derivative is coordinated to ruthenium as the ligand $L_1$. The substituents $R_1$ to $R_6$ of the ligand $L_1$ are each independently any one of a hydrogen atom, and a linear or branched alkyl group having a carbon number of 1 or more and 4 or less. The carbon number of the substituents $R_1$ to $R_6$ is thus defined in consideration of a vapor pressure of the ruthenium complex. If the carbon number is excessively large, it is concerned that the vapor pressure may be lowered.

With respect to the substituents of the ligand $L_1$, it is preferable that all of the substituents $R_1$ to $R_6$ are a hydrogen atom, or that $R_1$ is an ethyl group, and $R_2$ to $R_6$ are a hydrogen atom. This is for stabilizing the structure of the complex to obtain suitable thermal stability.

In the ruthenium complex applied in the present invention, in addition to a trimethylenemethane used as the ligand $L_1$ described above, benzene or a benzene derivative is coordinated to ruthenium as the ligand $L_2$. A benzene is applied as the ligand $L_2$ in the present invention for obtaining appropriate stability of the ruthenium complex.

The substituents $R_7$ to $R_{12}$ of the ligand $L_2$ are each independently any one of a hydrogen atom, and a linear or branched alkyl group having a carbon number of 1 or more and 4 or less. The carbon number of the substituents $R_7$ to $R_{12}$ is thus defined in consideration of the vapor pressure of the complex in the same manner as in the case of the ligand $L_1$.

With respect to the substituents $R_7$ to $R_{12}$, it is preferable that all of $R_7$ to $R_{12}$ are a hydrogen atom, that $R_7$ is a methyl group and $R_8$ to $R_{12}$ are a hydrogen atom, that $R_7$ is an ethyl group and $R_8$ to $R_{12}$ are a hydrogen atom, or that $R_7$ is a methyl group, $R_{10}$ is a 1-methylethyl group (isopropyl group), and $R_8$, $R_9$, $R_{11}$ and $R_{12}$ are a hydrogen atom. This is for obtaining suitable thermal stability of the structure of the complex.

With respect to the ruthenium complex according to the present invention described above, specific examples of the preferable complex are shown in the following table.

TABLE 1

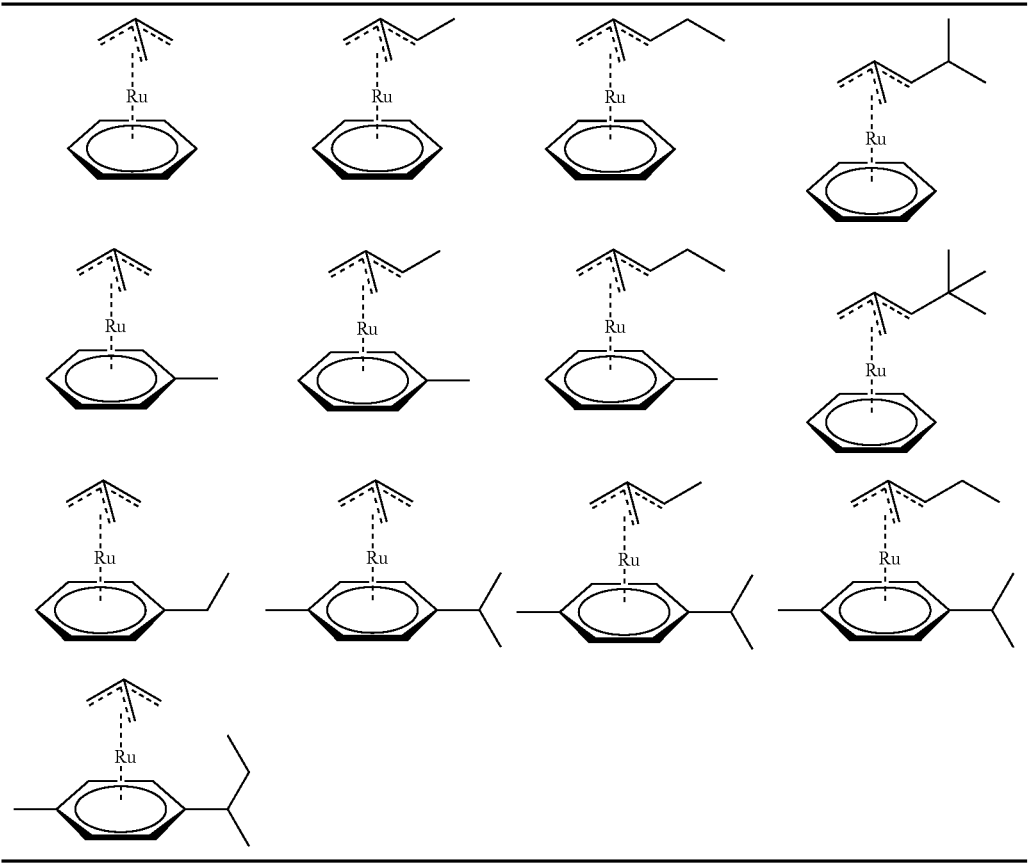

A chemical deposition method of a ruthenium-containing thin film to which the raw material for chemical deposition according to the present invention is applied will now be described. In the chemical deposition method according to the present invention, the raw material containing a ruthenium complex as described above is vaporized by heating to generate a raw material gas, and the ruthenium complex contained in the raw material gas is decomposed by heating on a substrate surface to form a ruthenium thin film.

With respect to a form of a raw material for the chemical deposition method, the ruthenium complex applied in the present invention is in a liquid state at normal temperature. Accordingly, in the chemical deposition method of the present invention, the raw material can be directly vaporized by heating. Alternatively, the raw material can be dissolved in an appropriate solvent to obtain a solution, and the solution can be heated to obtain a raw material gas. A heating temperature of the raw material is preferably 40° C. or more and 100° C. or less.

The vaporized raw material is usually transported together with a carrier gas onto a substrate as the raw material gas. For the ruthenium complex of the present invention, an inert gas (such as argon or nitrogen) is preferably used as the carrier gas.

For the raw material for chemical deposition according to the present invention, a reaction gas is preferably used. This is for effectively decomposing the ruthenium complex so as not to cause impurities such as carbon to remain in a resultant ruthenium-containing thin film. In the present invention, a reducing gas species such as hydrogen, ammonia, hydrazine, formic acid, or carbon monoxide can be applied as the reaction gas. It is a characteristic of the present invention that a reducing gas such as hydrogen can be used as the reaction gas. In the present invention, a ruthenium-containing thin film can be formed even if a gas species containing an oxygen atom, such as oxygen or ozone, is not used. It is noted that the reaction gas can work also as the carrier gas. The reaction gas is mixed with the vaporized ruthenium complex, and the carrier gas to be supplied, if necessary, onto a substrate.

In the present invention, however, application of oxygen as the reaction gas is not excluded. In film formation of a ruthenium compound thin film of a ruthenium oxide or the like, an oxygen gas can be applied as the reaction gas. Furthermore, the raw material for chemical deposition according to the present invention can be formed into a ruthenium-containing thin film by heating alone without using a reaction gas.

In use of the raw material for chemical deposition containing a ruthenium complex of the present invention, the film formation can be performed at a comparatively low temperature. A film forming temperature employed in the film formation is preferably 150° C. or more and 300° C. or less regardless of the use of the reaction gas. When the temperature is less than 150° C., a film forming reaction is difficult to proceed, and the film formation cannot be efficiently performed. On the other hand, when the temperature is too high, it is concerned that impurities may be mixed to lower the purity of a resultant film. It is noted that the film forming temperature is usually controlled in accordance with a heating temperature of a substrate.

Advantageous Effects of Invention

As described above, a ruthenium complex that constitutes a raw material for chemical deposition according to the present invention has suitable thermal stability falling within a range required of the raw material for chemical deposition because a ligand coordinated to ruthenium is suitably selected. With respect to the thermal stability, the ruthenium complex of the present invention has stability appropriate for being dealt with as a raw material for chemical deposition. In addition, it also has a suitably high vapor pressure because the ligand and substituents thereof are regulated.

In addition, reactivity of the raw material for chemical deposition according to the present invention is appropriately regulated, and hence a ruthenium-containing thin film can be produced even if a reducing gas such as hydrogen is used as a reaction gas. Here, contamination of the ruthenium-containing thin film thus formed with impurities such as carbon is prevented. Furthermore, it is not indispensable to use oxygen, ozone or the like as the reaction gas, and hence, there is no need to fear oxidative damage of a substrate.

Owing to these effects, the raw material for chemical deposition according to the present invention is useful for electrode formation in various semiconductor devices that have been highly miniaturized in recent years.

DESCRIPTION OF EMBODIMENTS

Figure 1:
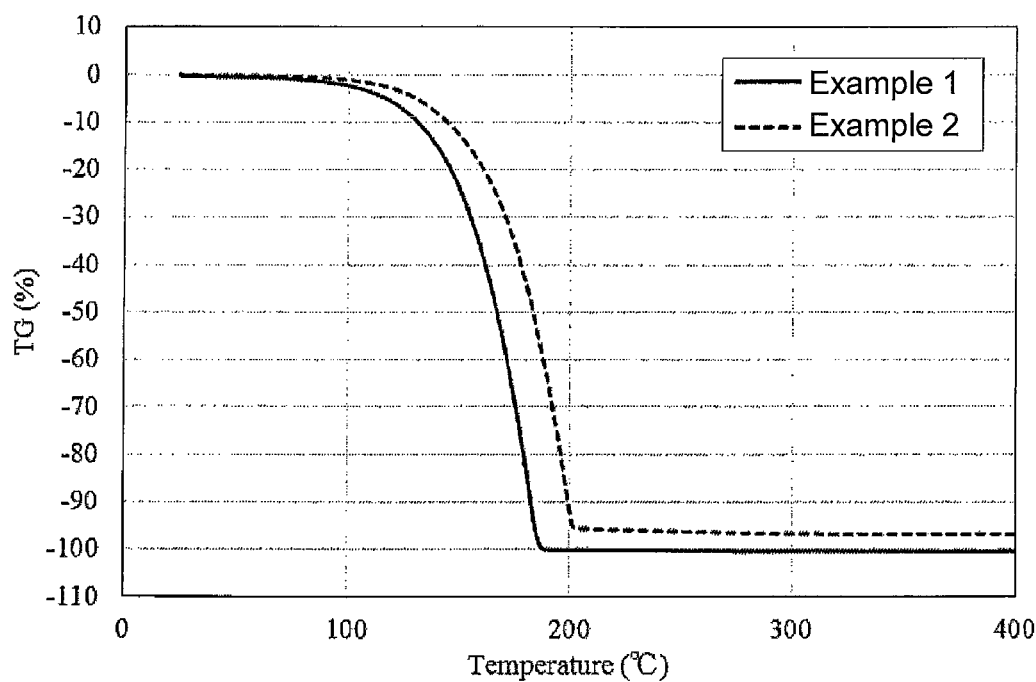
FIG. 1 is a diagram showing the results of TG-DTA of ruthenium complexes of Examples 1 and 2 performed under a nitrogen atmosphere.

Now, the best embodiment of the present invention will be described. In the present embodiment, two ruthenium complexes respectively using a trimethylenemethane derivative and a benzene as ligands were synthesized, thermal characteristics of the complexes were evaluated, and a film formation test for forming a ruthenium thin film was carried out.

Synthesis of Complexes

Example 1: Synthesis of (Methylene-1,3-propanediyl)[1-methyl-4-(1-methylethyl)benzene]ruthenium As a ruthenium complex of Example 1, (methylene-1,3-propanediyl)[1-methyl-4-(1-methylethyl)benzene]ruthenium having the following structural formula was synthesized.

[Chemical Formula 5]

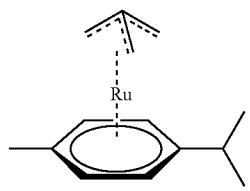

12.24 g (20 mmol) of di-μ-chlorodichlorobis[1-methyl-4-(1-methylethyl)benzene]diruthenium, 6.0 g (60 mmol) of 3-chloro-2-(chloromethyl)-1-propene, and 3.89 g (160 mmol) of magnesium were placed in a flask holding 320 ml of tetrahydrofuran (THF) as a solvent followed by reaction at room temperature for 3 hours. After the reaction, the solvent was distilled off under reduced pressure, and purification was conducted using an alumina column containing hexane as a developer solvent. Distillation purification was further conducted to obtain 4.0 g (13.8 mmol) of a target product of (methylene-1,3-propanediyl)[1-methyl-(1-methylethyl)benzene]ruthenium (yield: 35%). At this point, the reaction formula is as follows:

[Chemical Formula 6]

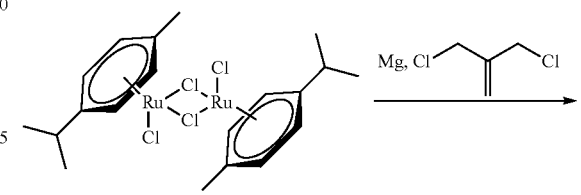

Example 2: Synthesis of Benzene(methylene-1,3-propanediyl)ruthenium

As a ruthenium complex of Example 2, benzene(methylene-1,3-propanediyl)ruthenium having the following structural formula was synthesized.

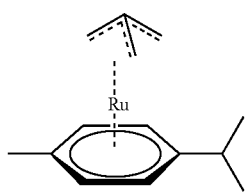

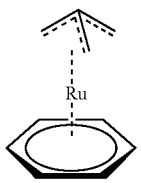

[Chemical Formula 7]

0.45 g (0.89 mmol) of bis(benzene)di-μ-chlorodichlorodiruthenium and 0.8 g (2.10 mmol) of 2-methylene-1,3-bis(trimethylstannyl)propane were placed in a flask holding 50 ml of tetrahydrofuran (THF) as a solvent, followed by reaction at room temperature for 30 hours. After the reaction, the solvent was distilled off under reduced pressure, and purification was conducted using an alumina column containing toluene as a developer solvent. Recrystallization from pentane was further conducted to obtain 0.18 g (0.77 mmol) of a target product of benzene(methylene-1,3-propanediyl)ruthenium (yield: 42%). At this point, the reaction formula is as follows:

[Chemical Formula 8]

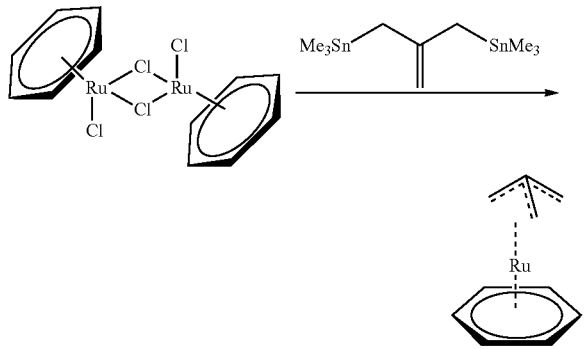

Comparative Example: Synthesis of Bis(ethylcyclopentadienyl)ruthenium

As a Comparative Example of the ruthenium complexes of Examples 1 and 2, bis(ethylcyclopentadienyl)ruthenium having the structural formula of the above-described Chemical Formula 1 was synthesized. 28.04 g (0.43 mol) of a zinc powder, 9.3 g (0.10 mol) of ethylcyclopentadiene, and 10.94 g (0.04 mol) of ruthenium trichloride were placed in a flask holding 131.5 ml of ethanol as a solvent, followed by reaction at −35° C. The resultant reaction solution was extracted with hexane and purified to obtain 11.74 g (0.04 mmol) of a target product of bis(ethylcyclopentadienyl)ruthenium (yield: 94%). At this point, the reaction formula is as follows:

[Chemical Formula 9]

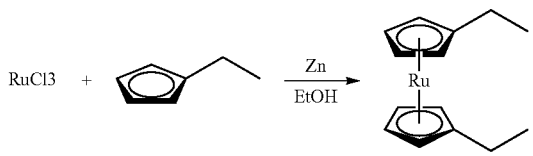

[Differential Scanning Calorimetry]

The ruthenium complexes of Examples 1 and 2 synthesized in the present embodiment were subjected to differential scanning calorimetry (DSC) to estimate a decomposition temperature. For analysis, a differential scanning calorimeter (DSC3500-ASC manufactured by NETZSCH) was used. A sealable aluminum pan was filled with a complex sample (weight: 1 mg), and DSC was observed under nitrogen atmosphere at a temperature increasing rate of 10° C./min in a measurement temperature range of −50° C. to 400° C. Then, a decomposition temperature was estimated based on an exothermic reaction. As a result of the DSC, the decomposition temperature of the ruthenium complex of Example 1 was measured as 198° C. The decomposition temperature of the ruthenium complex of Example 2 was measured as 228° C. It was found that the ruthenium complex of Example 1 was lower in thermal stability and was easily decomposed.

The ruthenium complex of Comparative Example was also subjected to the DSC, and the decomposition temperature of the complex of Comparative Example was 364° C. It was thus confirmed that the decomposition temperatures of the ruthenium complexes of Examples 1 and 2 were largely lower than that of the ruthenium complex of Comparative Example.

[Thermogravimetry]

The ruthenium complexes of Examples 1 and 2 were subjected to thermogravimetry-differential thermal analysis (TG-DTA) under nitrogen atmosphere and under hydrogen atmosphere respectively to examine decomposition characteristics in more detail. In this test, TG-DTA2000SA manufactured by BRUKER was used as an analysis apparatus, an aluminum cell was filled with a ruthenium complex sample (sample weight: 5 mg), and weight change was observed at a temperature increasing rate of 5° C./min in a measurement temperature range of room temperature to 400° C.

The measurement results of the ruthenium complexes of Examples 1 and 2 performed with TG-DTA under nitrogen atmosphere are illustrated in FIG. 1. According to the results, the complex of Example 1 is vaporized without forming a residue up to 188° C. It is thus found that this complex is thermally decomposed at 188° C. or more. On the other hand, vaporization of the complex of Example 2 is completed when the temperature is increased to 200° C. It is deemed that this complex is thermally decomposed at 200° C. or more. The temperatures of thermal decomposition estimated based on this thermogravimetry accord with the results of the DSC described above.

Figure 2:
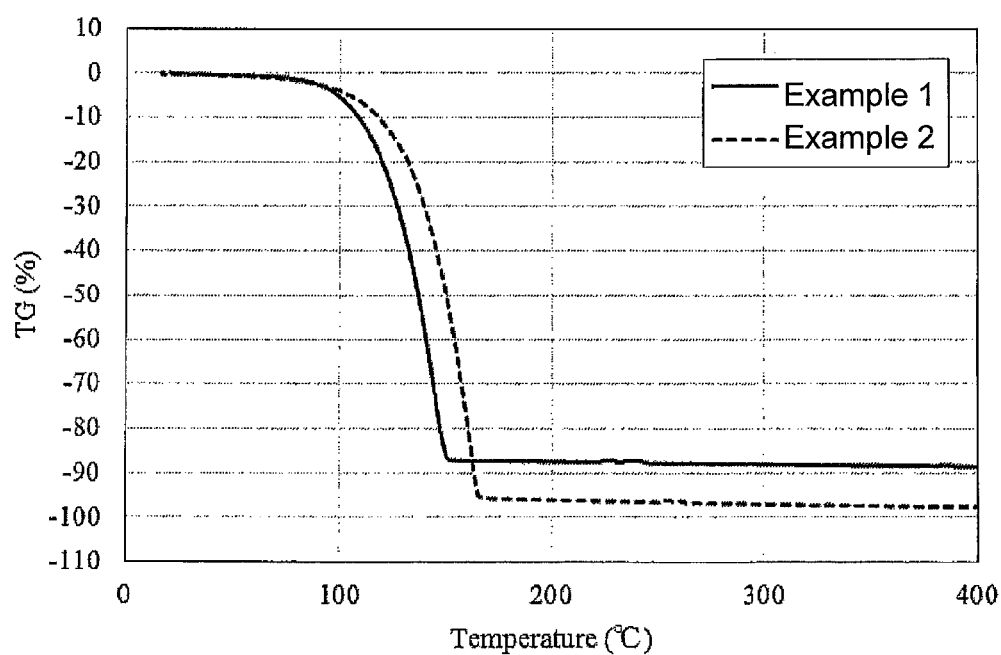
FIG. 2 is a diagram showing the results of TG-DTA of the ruthenium complexes of Examples 1 and 2 performed under a hydrogen atmosphere.

The measurement results of the ruthenium complexes of the respective Examples performed under hydrogen atmosphere with TG-DTA are illustrated in FIG. 2. Under hydrogen atmosphere, the vaporization of the ruthenium complex of Example 1 is completed at 148° C. with a residue formed. The vaporization of the ruthenium complex of Example 2 is completed at 172° C. with a residue formed. It is thus understood that both the complexes are vaporized and thermally decomposed at a lower temperature when the hydrogen atmosphere is employed.

Based on the results of FIGS. 1 and 2, there is no specific peak during the vaporization in thermogravimetric curves of the complexes of Examples 1 and 2. Therefore, it can be confirmed that both the complexes are smoothly vaporized by heating to an appropriate temperature. Also under hydrogen atmosphere, a vaporization characteristic of similar trends was found. In comparison between Examples 1 and Example 2, however, it is deemed that the vaporization characteristic is better in Example 1. This is because the complex of Example 1 is reduced in weight at a lower temperature and the vaporization is completed at a lower temperature.

Weight reduction observed in thermogravimetry encompasses both weight reduction due to vaporization and weight reduction due to decomposition. A residue is formed through decomposition. Accordingly, it is deemed that a complex whose weight reduction is completed at a lower temperature and a complex forming a larger amount of a residue are complexes easily decomposed. When the measurement results obtained under hydrogen atmosphere of FIG. 2 are examined from this point of view, the complex of Example 1 forms a larger amount of residue at a lower temperature (148° C.) as compared with the complex of Example 1. Therefore, it is deemed that the complex of Example 1 is more easily decomposed under hydrogen atmosphere, and is a suitable complex.

[Film Formation Test]

Next, each of the ruthenium complexes of Examples 1 and 2 and Comparative Example was used as a raw material to form a ruthenium thin film with a CVD apparatus (hot wall CVD apparatus). Film formation conditions are described below, and after forming a ruthenium thin film, a film thickness and a specific resistance of the thin film were measured. For measuring the film thickness, a result observed with EA1200VX, manufactured by Hitachi High-Tech Science Corporation was used. As a method/conditions for measuring a specific resistance, MCP-T370, manufactured by Mitsubishi Chemical Analytech Co Ltd. was used for performing the measurement by a four probe method. The results of this film formation test are shown in Table 2.

Substrate: Si

Film forming temperature: 250° C.

Sample temperature (vaporization temperature): 55° C.

Film forming pressure: 5 torr

Reaction gas (carrier gas): hydrogen gas

Gas flow rate: 20 sccm

Film forming time: 30 min

TABLE 2

|  | Ruthenium Thickness | Specific Resistance |
| --- | --- | --- |
| Example 1 | 7.8 nm | 36.4 μΩ · cm |
| Example 2 | 13.9 nm | 60.0 μΩ · cm |
| Comparative Example | — | — |

It was confirmed, based on Table 2, that a ruthenium thin film can be formed with a hydrogen gas used as a reaction gas when the ruthenium complexes of Examples 1 and 2 were used. On the contrary, when the ruthenium complex of Comparative Example was used, a ruthenium thin film failed to be formed with a hydrogen gas, and a specific resistance could not be measured.

Next, the ruthenium complex of Example 1 was applied to perform a film formation test with a film forming temperature set to 150° C. and 200° C. The film formation conditions were the same as those described above, and a film thickness and a specific resistance of a resultant ruthenium thin film were measured in the same manner as described above. The results of this film formation test are shown in Table 3. In Table 3, the results of the film formation of Example 1 at 250° C. (Table 2) are also shown.

TABLE 3

| Film Forming Temperature | Ruthenium Thickness | Specific Resistance |
| --- | --- | --- |
| 250° C. | 7.8 nm | 36.4 μΩ · cm |
| 200° C. | 8.7 nm | 55.6 μΩ · cm |
| 150° C. | 11.4 nm | 86.6 μΩ · cm |

It is understood, from Table 3, that the ruthenium complex of Example 1 can be a raw material compound of a ruthenium thin film formed in a wide temperature range of 150° C. to 250° C. with a hydrogen gas used as a reaction gas. In particular, it was confirmed to be applicable to low temperature film formation at 150° C.

INDUSTRIAL APPLICABILITY

In a raw material for chemical deposition according to the present invention, a ruthenium complex constituting the raw material has thermal stability in an appropriate range, and hence, a ruthenium-containing thin film having a good quality can be produced even if a hydrogen gas is used as a reaction gas. The present invention is suitably used as a thin film electrode material of a semiconductor device such as a DRAM or an FERAM.

The invention claimed is:

1. A raw material for chemical deposition for producing a ruthenium thin film or a ruthenium compound thin film by a chemical deposition method, comprising a ruthenium complex represented by the following Chemical Formula 1:

$$RuL_1L_2 \qquad [\text{Chemical Formula 1}]$$

wherein ligands $L_1$ and $L_2$ coordinated to ruthenium are represented by the following Chemical Formula 2:

[Chemical Formula 2]

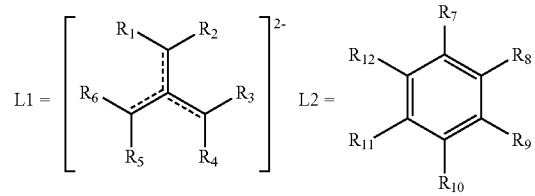

wherein $R_1$ to $R_{12}$, which are substituents of the ligands $L_1$ and $L_2$, are each independently any one of a hydrogen atom, and a linear or branched alkyl group having a carbon number of 1 or more and 4 or less.

2. The raw material for chemical deposition according to claim 1, wherein in substituents $R_1$ to $R_6$ of the ligand $L_1$, all of $R_1$ to $R_6$ are a hydrogen atom, or $R_1$ is an ethyl group and $R_2$ to $R_6$ are a hydrogen atom.

3. The raw material for chemical deposition according to claim 2, wherein in substituents $R_7$ to $R_{12}$ of the ligand $L_2$, all of $R_7$ to $R_{12}$ are a hydrogen atom, $R_7$ is a methyl group and $R_8$ to $R_{12}$ are a hydrogen atom, $R_7$ is an ethyl group and $R_8$ to $R_{12}$ are a hydrogen atom, or $R_7$ is a methyl group, $R_{10}$ is a 1-methylethyl group, and $R_8$, $R_9$, $R_{11}$ and $R_{12}$ are a hydrogen atom.

4. The raw material for chemical deposition according to claim 1, wherein in substituents $R_7$ to $R_{12}$ of the ligand $L_2$, all of $R_7$ to $R_{12}$ are a hydrogen atom, $R_7$ is a methyl group and $R_8$ to $R_{12}$ are a hydrogen atom, $R_7$ is an ethyl group and $R_8$ to $R_{11}$ are a hydrogen atom, or $R_7$ is a methyl group, $R_{10}$ is a 1-methylethyl group, and $R_8$, $R_9$, $R_{11}$ and $R_{12}$ are a hydrogen atom.

5. A chemical deposition method of a ruthenium thin film or a ruthenium compound thin film, wherein the method comprising vaporizing a raw material comprising a ruthenium complex to obtain a raw material gas, and introducing the raw material gas onto a substrate surface while heating to decompose the ruthenium complex, wherein the raw material for chemical deposition defined in claim 1 is used as the raw material.

6. The chemical deposition method according to claim 5, wherein a reducing gas is used as a reaction gas.

7. A chemical deposition method of a ruthenium thin film or a ruthenium compound thin film, wherein the method comprising vaporizing a raw material comprising a ruthenium complex to obtain a raw material gas, and introducing the raw material gas onto a substrate surface while heating to decompose the ruthenium complex, wherein the raw material for chemical deposition defined in claim 2 is used as the raw material.

8. A chemical deposition method of a ruthenium thin film or a ruthenium compound thin film, wherein the method comprising vaporizing a raw material comprising a ruthenium complex to obtain a raw material gas, and introducing the raw material gas onto a substrate surface while heating to decompose the ruthenium complex, wherein the raw material for chemical deposition defined in claim 4 is used as the raw material.

* * * * *